US007247275B2

(12) United States Patent
Caldwell et al.

(10) Patent No.: US 7,247,275 B2
(45) Date of Patent: Jul. 24, 2007

(54) GEL EXTRACTION DEVICE

(76) Inventors: Jeremy Scot Caldwell, 2031 Edinburg Ave., Cardiff by the Sea, CA (US) 92007; Dale R Caldwell, 7925 Kildare Ave., Skokie, IL (US) 60076; Leon C. Clouser, Jr., 581 S. Finley Rd., Lombard, IL (US) 60148

( * ) Notice: Subject to any disclaimer, the term of this patent is extended or adjusted under 35 U.S.C. 154(b) by 578 days.

(21) Appl. No.: 10/871,655

(22) Filed: Jun. 21, 2004

(65) Prior Publication Data
US 2005/0281709 A1    Dec. 22, 2005

(51) Int. Cl.
*B01L 3/02* (2006.01)

(52) U.S. Cl. .................. 422/100; 422/104; 83/167; 83/919; 204/606; 204/613

(58) Field of Classification Search .......... 422/99–101, 422/104; 83/167, 919; 204/450, 456, 462, 204/466, 613, 606
See application file for complete search history.

(56) References Cited

U.S. PATENT DOCUMENTS

| 3,949,471 | A | * | 4/1976 | Cawley ............... 30/123.3 |
| 4,341,735 | A | * | 7/1982 | Seifried ................ 422/66 |
| 4,696,298 | A | * | 9/1987 | Higgins et al. ........... 606/171 |
| 5,188,599 | A | * | 2/1993 | Botich et al. ............. 604/110 |
| 5,217,591 | A | | 6/1993 | Gombocz et al. |
| 5,289,727 | A | | 3/1994 | Earle et al. |
| 5,343,771 | A | * | 9/1994 | Turriff et al. ............. 73/864.44 |
| 5,413,115 | A | | 5/1995 | Baldwin |
| 5,476,017 | A | | 12/1995 | Pinto et al. |
| 5,587,062 | A | | 12/1996 | Togawa et al. |
| 5,638,170 | A | * | 6/1997 | Trinka et al. ............. 356/244 |
| 6,090,077 | A | * | 7/2000 | Shaw ................ 604/195 |
| 6,342,143 | B1 | * | 1/2002 | Minden ................ 204/462 |
| 6,393,926 | B1 | | 5/2002 | Bowersox, Jr. |
| 6,482,303 | B2 | * | 11/2002 | Anderson et al. ........... 204/462 |
| 6,526,320 | B2 | * | 2/2003 | Mitchell ............... 607/101 |
| 6,565,728 | B1 | * | 5/2003 | Kozulic ................ 204/606 |
| 6,702,990 | B1 | | 3/2004 | Camacho et al. |
| 6,835,193 | B2 | * | 12/2004 | Epstein et al. ........... 604/507 |
| 6,840,291 | B2 | * | 1/2005 | Caizza et al. ............. 141/25 |
| 7,093,508 | B2 | * | 8/2006 | Harris ................ 73/864.44 |
| 2004/0101974 | A1 | * | 5/2004 | Fagerstam .............. 436/518 |
| 2006/0099114 | A1 | * | 5/2006 | Caldwell et al. ............ 422/99 |

FOREIGN PATENT DOCUMENTS

JP    2002307 388    10/2002

\* cited by examiner

*Primary Examiner*—Jill Warden
*Assistant Examiner*—Dwayne K. Handy
(74) *Attorney, Agent, or Firm*—Barbara R. Greenberg

(57) ABSTRACT

A gel extraction device comprising a hollow cutting member and a plunger ejector member. The hollow cutting member has a proximal tubular body terminating at one end in a circular rim having oppositely disposed spring engaging structures and a distal sloped transition portion ending in a rectangular receptacle and a tapered end portion with a sharp perimeter cutting edge. The plunger ejector member has a proximal cap atop and connected to a split stem portion having outer legs with shoulder stop extensions; an inner ribbon spring leg having a distal end inserted into a spring engaging structure in the assembled device; and a solid rectangular distal portion. In a second embodiment the split end portion is replaced by a stem having a plurality of lateral protrusions and a coiled spring is placed within the hollow cutting member tubular body. A third embodiment is a hybrid of the first two embodiments.

19 Claims, 8 Drawing Sheets

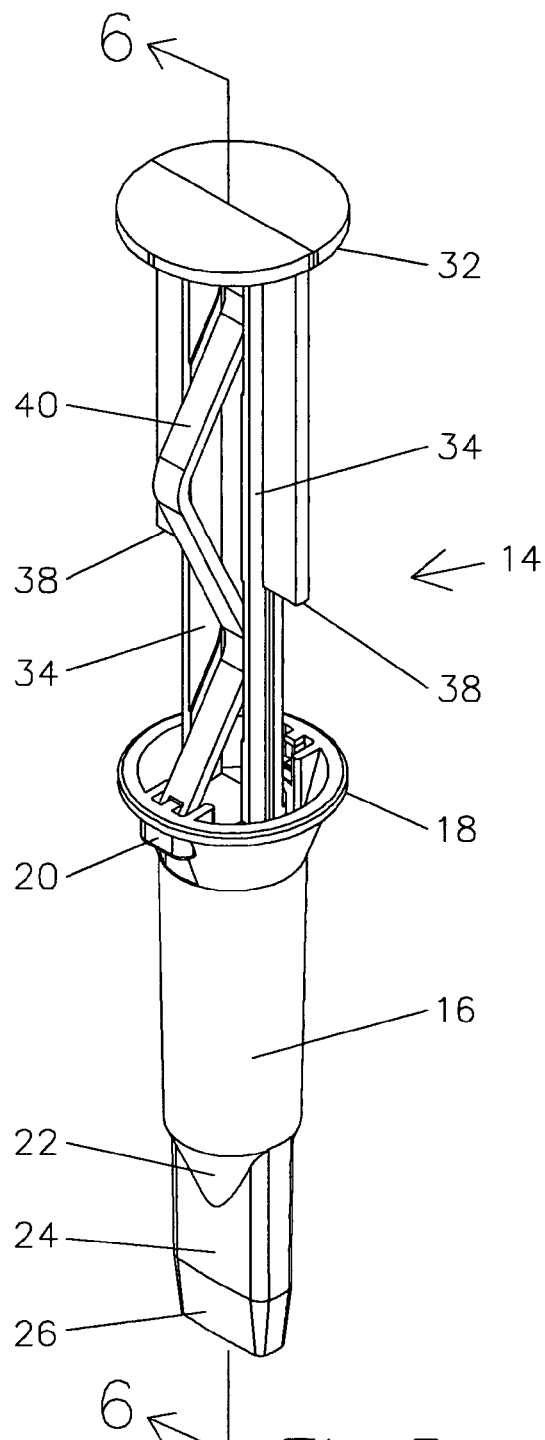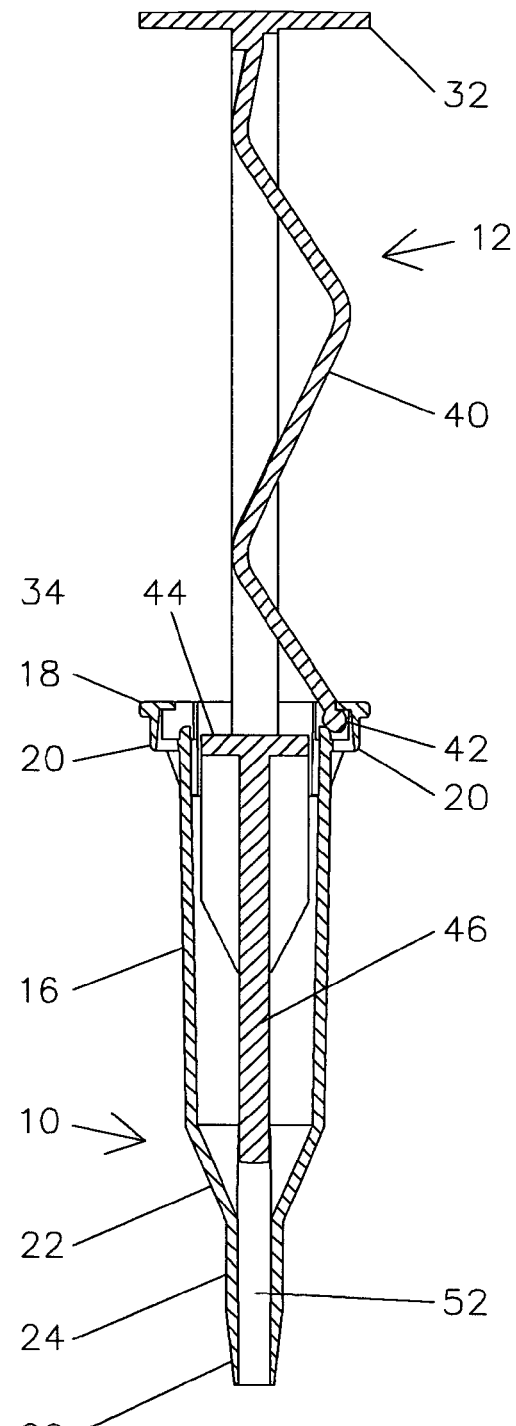
Fig. 5
Fig. 6

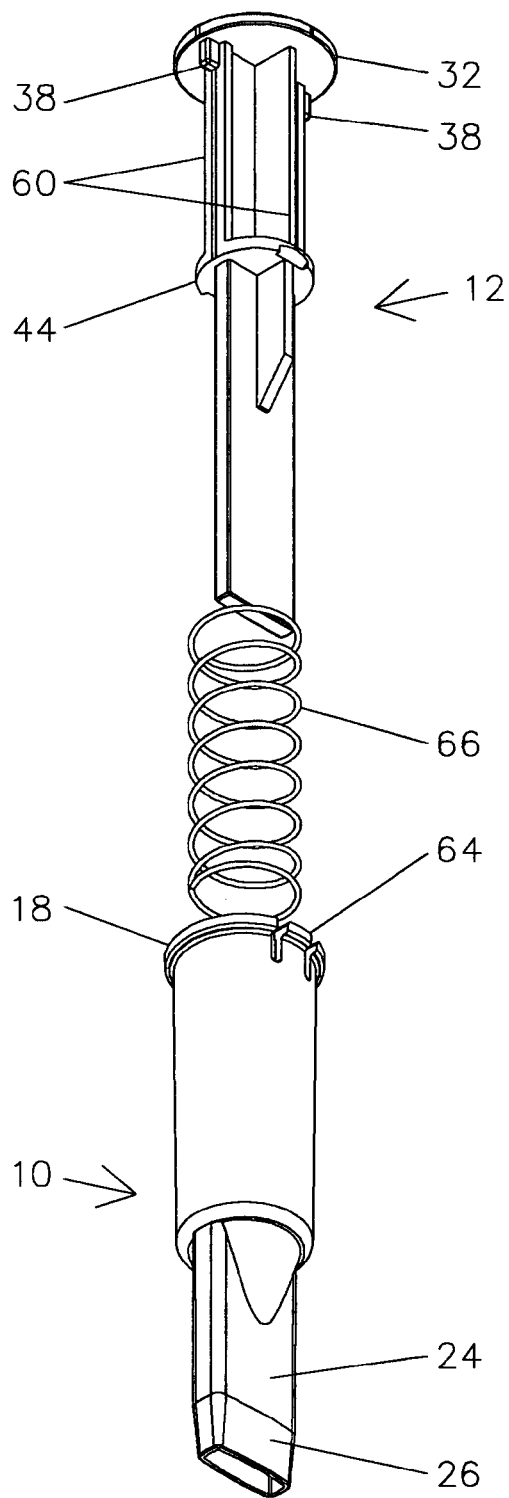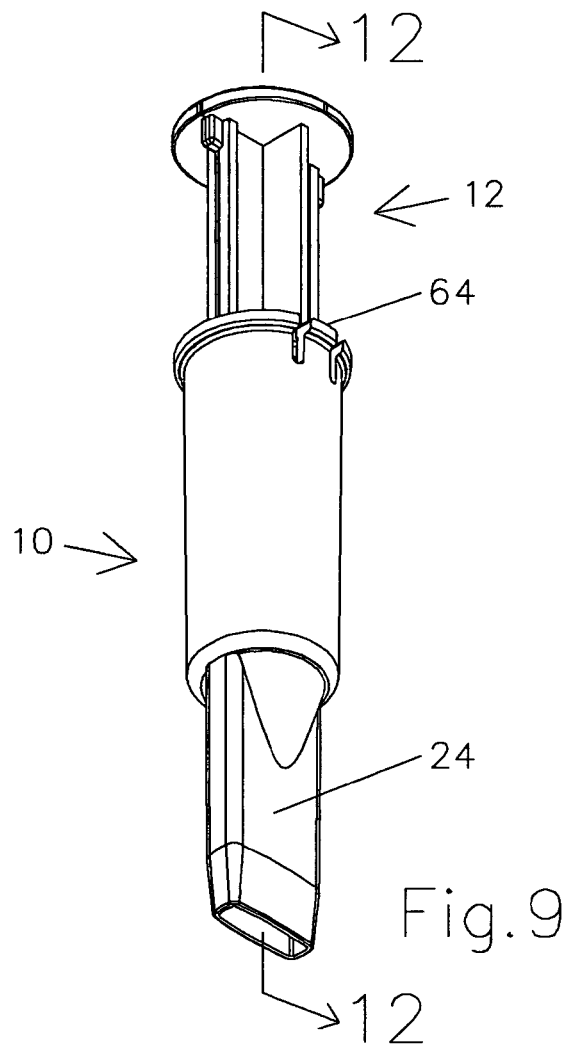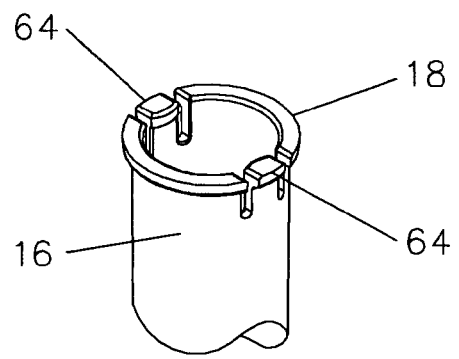

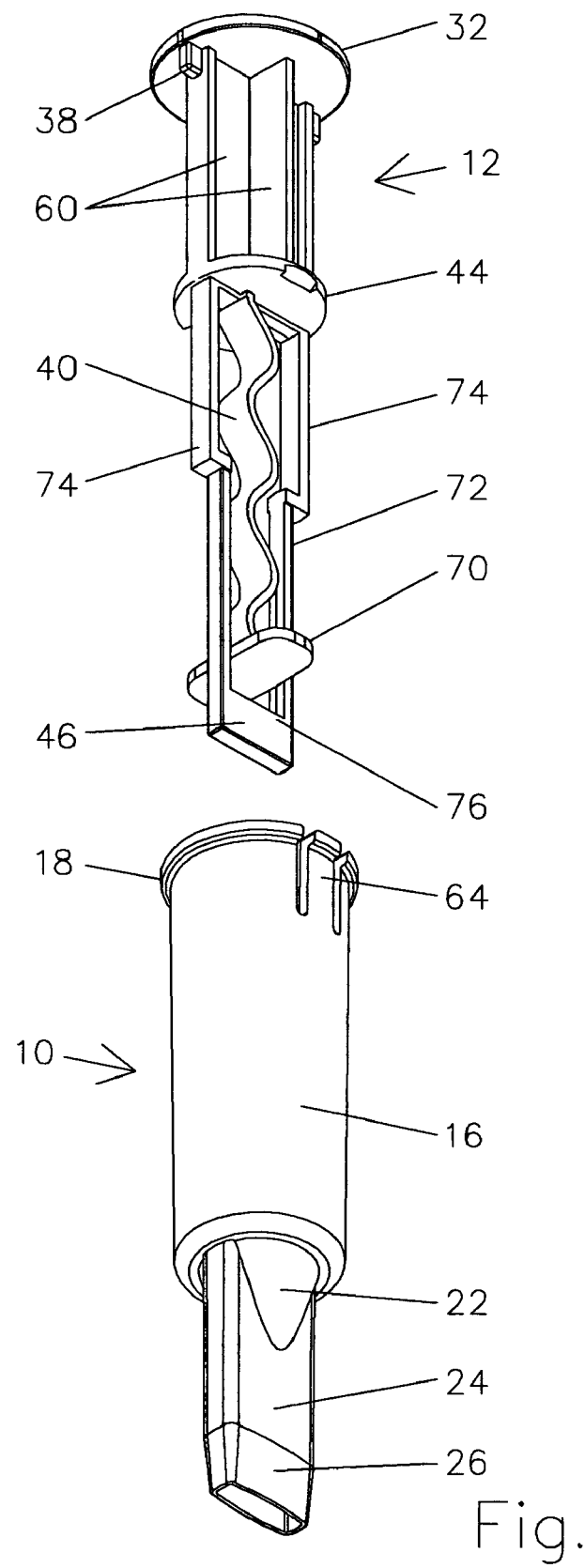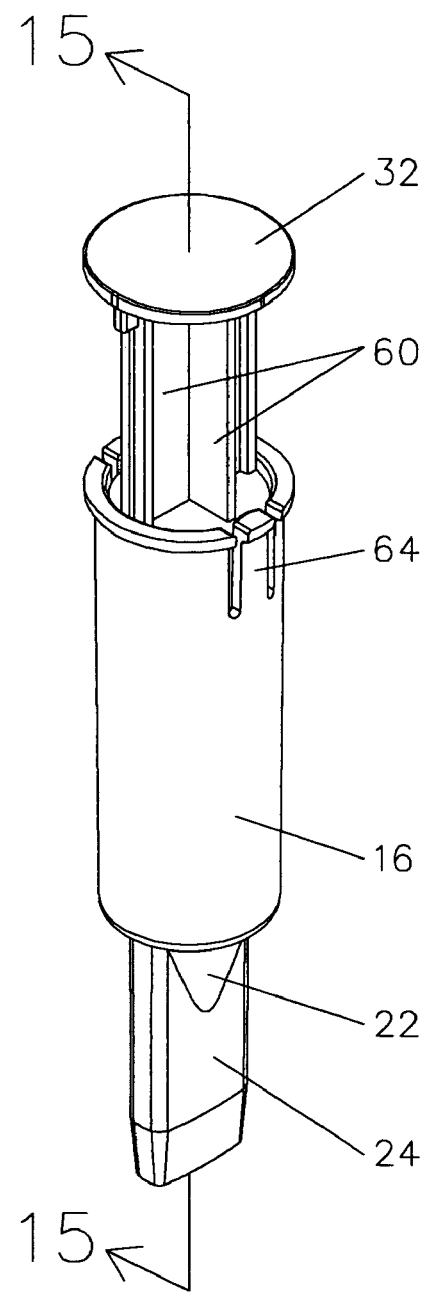
Fig.13
Fig.14

GEL EXTRACTION DEVICE

BACKGROUND OF THE INVENTION

Gel electrophoresis is used extensively in the field of biotechnology to separate target biological macromolecules (biomolecules), such as DNA, RNA, or protein from a mixture of biomolecules. This analytical tool, which utilizes a gel matrix to achieve separation of biomolecules, is used at the research level and also during the manufacturing and quality assurance testing of biomolecules. It is often desirable to remove a target biomolecules from a gel polymer for further analysis. This invention relates to a device for transferring target biomolecules from the gel matrix to a container, such as an Eppendorf tube, for further analysis.

The excision of gel slices from an electrophoresis gel matrix can be effected by using a razor blade or scalpel to cut away the gel portion corresponding to the target biomolecules and using tweezers or the equivalent to transfer a resultant gel slice to a receiving container. One important objective of a biotechnologist is a high level of experimental result reproducibility. Unfortunately the manual blade technique is susceptible to a high degree of technique related variability, which affects the reproducibility of results obtained in subsequent evaluations of the transferred target biomolecule.

Lack of uniformity of gel slices leads to significant variations in DNA purification yields. In a gel electrophoresis, macromolecules migrate to form bands. The migrations distance of each band in an electric field is determined by a band biomolecule size, shape, mass and charge. If a targeted biomolecule migrates to form a tight band, well separated from other biomolecules a blade excision procedure may be useful to extract a clean sample and repeat the process, if necessary. However, when a band is diffuse and not well separated from other biomolecules, the blade excision procedure has little chance of producing a clean, reproducible sample. Resulting variability can be caused by contaminating biomolecules and/or different isomers exhibiting different degrees of biological activity. In addition, differences in the sizes of excised bands can result in significant variability in follow-up activity assays.

Another disadvantage of the blade technique concerns a safety issue generally associated with sharp objects in general whereby users are susceptible to cuts. In addition, when blades are used to excise gel bands, a further potential health complication exists if the electrophoresis step is carried out with radioactively labelled biomolecules. A cut to a hand during the band excision process could result in a transfer of potentially dangerous radioactive material directly to a user's skin. Still another disadvantage of the blade technique is that it requires a separate means for transferring a blade excised gel slice to a suitable container. Tweezers are commonly used for this transfer where gel slice compression and biomolecule damage can occur. A final disadvantage of the blade technique is that blades and tweezers are generally used repeatedly, thereby potentially leading to contamination of subsequent excised gel slices.

The foregoing problems with a manual blade excision technique demonstrate the need for a user friendly devise for cutting and transferring gel slices to 1) easily extract and transfer a clean reproducible marcromolecule sample; 2) maximize the reproducibility of a band excision process; and 3) protect the user from blade related health dangers. Others have recognized the need for such a devise. In U.S. Pat. No. 6,565,728 Kozulic teaches a device used for cutting and recovering a selected gel piece from a larger gel mass. The gel piece is separated from the gel with a hollow member distal end cutting edge and remains in the hollow member distal end due to reduced hollow member internal pressure caused by the manual movement of a piston. An application of piston pressure decreases the hollow member distal end volume thereby increasing the pressure and releasing the gel piece for transfer to a suitable container for further analysis. In this invention, the gel extraction process is dependent on pressure changes in the gel extraction device. The present invention has no pressure change requirements. Here a sharp cutting edge simply cuts a gel slice which remains in a rectangular hollow receptacle until a manually spring controlled plunger head contact the retained gel slice, causing it to exit the device into a suitable container.

In U.S. Pat. No. 6,393,926, Bowersox teaches a method for sampling solid, liquid, and semi-solid bulk materials including gelatinous material. Here the objective is not to isolate a particular biomolecule but to isolate a sample representative of the mixture as a whole. A spring mechanism is used to retract a device's shaft assembly thereby decreasing an internal pressure which allows an external pressure to keep a selected sample in a collection cavity until the shaft assembly rests increasing internal pressure and releasing the sample. An o-ring is needed to insure collection cavity pressure changes. In opposition to the present invention, as in Kozulic, device internal pressure gradations are needed to both hold and eject a gel sample.

Minden (U.S. Pat. No. 6,342,143) teaches a cutting tool for multiple sample retrieval from electrophoretic gels whereby a spring loaded coupling shaft acts as a piston to move a plunger through a cutting tip to remove a cut band via internal pressure gradations. The spring loaded coupling shaft is connected to a computer in order to control movement of the coupling shaft and plunger. As in the Kozulic patent where a distance between the piston and wall of a lumen cavity is critical for maintaining an appropriate internal pressure, the internal pressure in the Minden patent is highly dependent upon a distance between a moving plunger and an axial passage. Pressure gradations are necessary to operate the device. Since it is unnecessary, the present invention is not designed to change internal pressures. In addition, the present invention does not involve a computer. It requires only one handed operation to efficiently extract clean gel samples in a reproducible fashion.

In U.S. Pat. No. 5,587,062 Togawa, et al. discloses a robotic apparatus for excising gel slices which uses an optical detector to detect gel migration patterns. The device's tubular cutting tool is adapted to be pressed against the gel causing a sliced gel slice to be packed inside the tool. The cutting tool can hold up to four excised gel slices. Ejection of the retained gel slices is achieved with compressed air. Togawa, et al, do not discuss the mechanism by which excised gel slices are retained in the cutting tool. Also, it is not clear whether the gel slices actually remain in the tubular cutting tool until the application of compressed air. However, the disclosure does provide that cutting tool is not designed to be an indispensable part of the invention and that a scalpel can be used to cut out the desired gel portions instead of a cutting tool. In the present invention, the cutting edge and the receptacle for holding the excised gel slices are indispensable parts of the device. The cutting edge is designed to ensure a clean excision of gel slices from a wide variety of gel strengths and thicknesses. The receptacle is designed to ensure proper seating of the excised gel slice to maximize frictional retention forces.

The present invention comprises a gel cutting extraction device capable of controlled one handed cutting and simple removing of clean samples from a wide variety of electrophoretic gels.

OBJECTS AND SUMMARY OF THE INVENTION

Accordingly, it is a primary objective of the present invention to provide a reliable gel slice extraction device capable of repeatedly cutting clean gel slices from a slab gel for further analysis of any biomolecules contained within an extracted gel slice.

Another primary objective of the present invention is to provide a reliable gel slice extraction device that retains an extracted gel slice by friction force rather than less reliable internal/external pressure variations.

Still another primary objective of the present invention is to provide a quick and easy single handed means for gel slicing and transferring.

In recognition of the fact that the strength and thickness of a slab gel varies with respect to the properties of embedded biomolecules undergoing electrophoretic separation, another objective of the present invention is to provide a device capable of isolating gel slices of varying strengths and thicknesses.

Another objective of the present invention is to provide a multi angle gel slicing device capable of cutting samples from most angles of insertion, mainly from a 90° angle desirable for a clean extraction.

Finally, a gel extraction device is provided with spring means for controlled gel slice removal.

In accordance with the invention, there is provided a gel slice extraction device that cleanly cuts a targeted gel matrix piece and retains the piece for transfer to an appropriate container, the device comprising a hollow cutting member and a plunger ejector member. The hollow cutting member has a tubular proximal portion that tapers gradually to a hollow rectangular distal portion ending in a sharp cutting edge. The tubular proximal portion is fitted with a rim having spring locking tabs for a ribbon spring reception. The plunger ejector includes a proximal end cap atop a split stem portion. Outer opposing legs of the split stem portion have shoulder extensions that act to stop plunger downward action. A middle leg serves as the ribbon spring providing spring action to control plunger ejector progress through the hollow cutting member. The split stem portion terminates in a disk where a solid rectangular distal portion begins. When the gel slice extraction device is assembled, the plunger ejection member rectangular distal portion is slidingly inserted into the hollow cutting member hollow rectangular distal portion and the ribbon spring is engaged by the spring locking tabs. When pressure is applied to the proximal end cap, the ribbon spring is compressed until the shoulder extensions reach the rim. In addition, the solid rectangular portion contacts an embedded gel slice and ejects the gel slice into a suitable container. Release of pressure on the end cap causes the ribbon spring to decompress and return to an at rest position drawing the rectangular distal portion away from the hollow rectangular distal portion sharp cutting edge. Upon return to the at rest position, the device can be re-used repeatedly to achieve the isolation of other gel slices.

In a second embodiment of the invention, the split end portion is replaced by a stem having a plurality of lateral protrusions arranged at right angles to each other. A coiled spring is placed within the hollow cutting member tubular body. Pressure applied to the proximal end cap compresses the coiled spring until the shoulder extensions reach the rim at which time the disk is below the rim. On spring decompression, flexible rim tabs hold the plunger ejection member within the hollow cutting member tubular body so the gel extraction device is ready for further use.

A third embodiment of the invention is a hybrid of the first and second embodiments. Here, the ribbon spring is contained within the hollow cutting member tubular body and the plunger ejector member has a stem with lateral protrusions arranged at right angles to each other.

DETAILED DESCRIPTION OF THE DRAWINGS

FIG. 5 is a perspective view of the fully assembled invention.

FIG. 6 is a cross sectional view taken through line 6-6 of FIG. 5.

FIG. 8 is an exploded perspective view of a second embodiment of the invention.

FIG. 9 is an assembled perspective view of a second embodiment of the invention.

FIG. 10 is a perspective view of flexible snap locks of a second embodiment of the invention.

FIG. 13 is an exploded perspective view of a third embodiment of the invention.

FIG. 14 is a perspective view of a third embodiment of the invention.

SPECIFICATION

Figure 1:
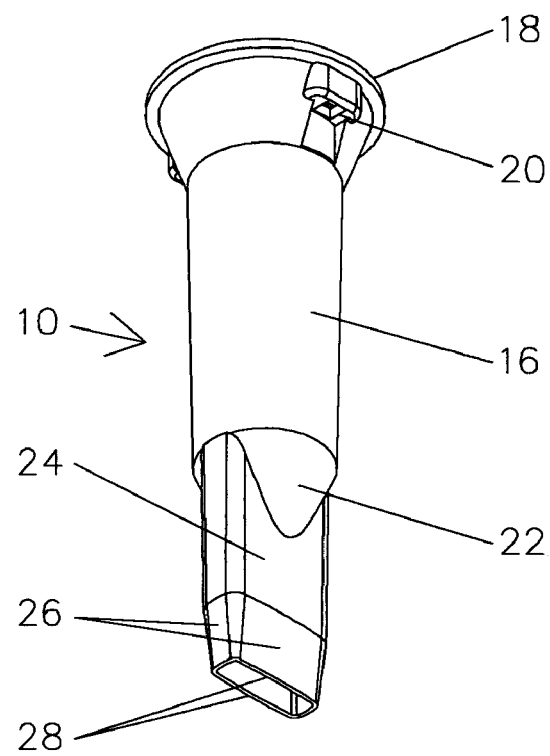
FIG. 1 is a perspective view of the hollow cutting member of the invention.
Figure 2:
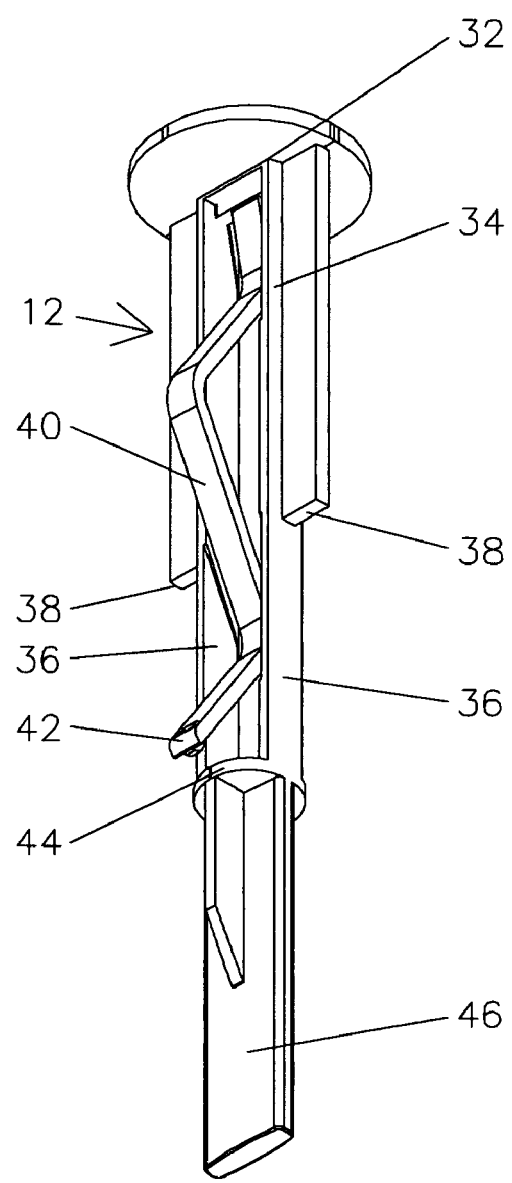
FIG. 2 is a perspective view of the plunger ejector member of the invention.

Referring now to FIGS. 1 and 2, a gel extraction device is described wherein like reference numerals refer to like elements throughout. Also, mutually related components of the present invention are depicted in FIGS. 1 and 2. FIG. 1 illustrates a hollow cutting member 10 that receives a plunger ejector member 12 as illustrated in FIG. 2 to comprise the gel extraction device 14 shown fully assembled in FIG. 5. The hollow cutting member 10 has a proximal tubular body 16 terminating in a circular rim 18, having a pair of oppositely disposed spring engaging structures 20. At an end opposite to the circular rim 18, the hollow cutting member 10 proximal tubular body 16 tapers gradually into a sloped transition portion 22 ending in a rectangular receptacle 24 shaped to accommodate rectangularly shaped gel slices, the typical shape of bands of biomolecules obtained by electrophoresis. The rectangular receptacle 24 terminates in a tapered end portion 26 with a perimeter cutting edge 28 that cleanly cuts gel slices from electrophoretic gels. The tapered end portion 26 is formed where opposite short sides and one long side of the rectangular receptacle 24 gradually move closer to each other terminating at the perimeter cutting edge 28. This configuration enhances gel slice contact with interior rectangular receptacle 24 tapered end portion 26 walls thus benefiting friction force gel slice retention. The perimeter cutting edge 28 is between 0.005 inch to 0.020 inch in thickness. Spring engaging structures 20 are oriented at approximately 90 degree angles to the rectangular receptacle 24 so that proper plunger ejection member 12 insertion can occur. In a preferred embodiment of the hollow cutting member 10, a transition from the proximal tubular body 16 to the rectangular receptacle 24 is achieved by the sloped transition portion 22 as shown perspectively in FIG. 1.

Figure 3:
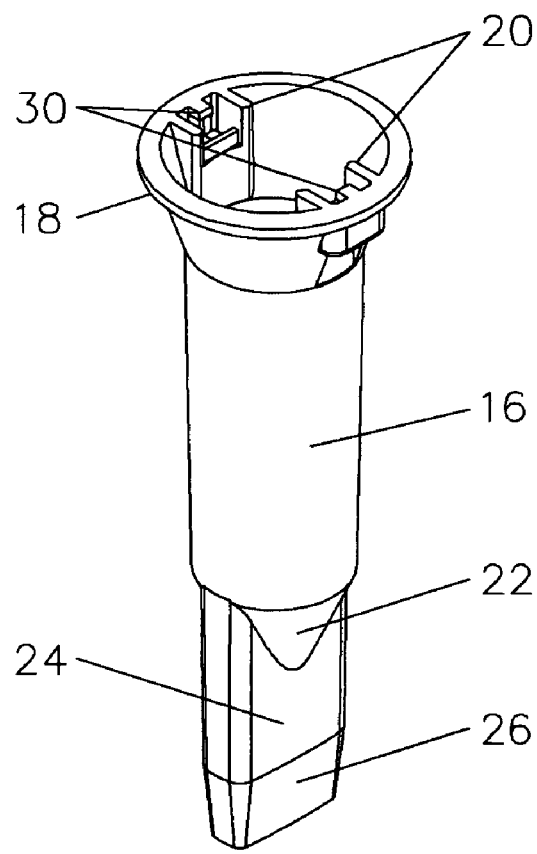
FIG. 3 is a top perspective view of the hollow cutting member rim of the invention.

In FIG. 3, a top view of the circular rim 18 shows the spring engaging structures 20 flush with the circular rim 18 and having centrally projected spring locking tabs 30 for spring engagement.

The plunger ejection member 12 shown perspectively in FIG. 2, comprises a proximal end cap 32 atop and connected to a split stem portion 34 consisting of outer legs 36 having shoulder extension stops 38 and an inner ribbon spring leg 40 having a free distal end 42. The outer legs terminate in a disk 44 where a solid rectangular distal portion 46 begins.

Figure 4:
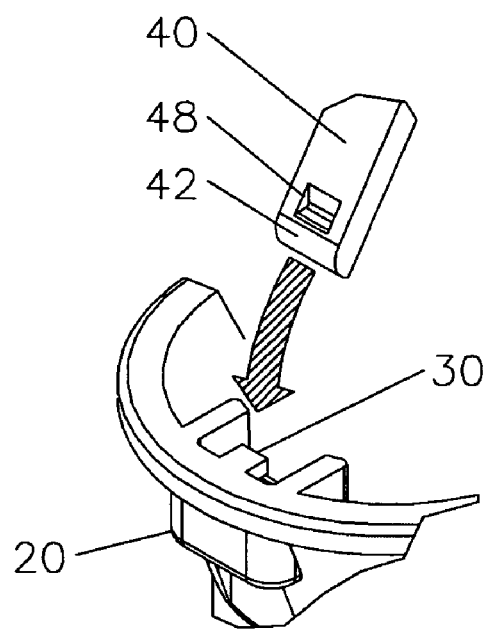
FIG. 4 is a perspective view of the hollow cutting member circular rim as related to the ribbon spring of the invention.

FIG. 4 illustrates a connection relationship between the inner ribbon spring leg 40 free distal end 42 and the spring engaging structures 20. The free distal end 42 is of sufficient size and is provided with a depression 48 to allow the free distal end 42 to snap under one of the spring locking tabs 30 and fit snugly into the spring engaging structure 20 thus connecting the plunger ejection member 12 to the hollow cutting member 10. When the ribbon spring leg 40 is engaged as is illustrated in FIG. 4, the gel extension device 14 is ready to begin a gel slice extraction.

In FIG. 6, a cross section taken through 6-6 of FIG. 5, an assembled gel extraction device 14, the solid rectangular distal portion 46 of the plunger ejection member 12 is comfortably seated within the hollow cutting member 10 proximal tubular body 16 and sloped transition portion 22 where the solid rectangular distal portion 46 can enjoy free movement to extend slightly below the perimeter sharp cutting edge 26 during a gel slice rejection and to retract within the hollow rectangular receptacle 20 in a ready position. In the ready position as illustrated in FIG. 6, the rectangular receptacle defines a distal space 52 where gel slice retention occurs. There is no need for a tight plunger ejector member 12 fit within the hollow cutting member 10 since gel slice retention occurs by friction force and not by a decrease in internal pressure.

As the gel extraction device 14 is assembled, as seen in FIG. 5, the plunger ejection member 12 inner ribbon spring leg 40 free distal end 42 is inserted into the spring engaging structure 20 which acts as a guide to simultaneously direct the solid rectangular distal portion 46 slidingly into the hollow cutting member 10 rectangular receptacle 24. The solid rectangular distal portion 46 has an outer surface that is adjacent to a rectangular receptacle inner surface separated by a space sufficient to allow free movement of the solid rectangular distal portion 46 through the rectangular receptacle 24.

Figure 7A:
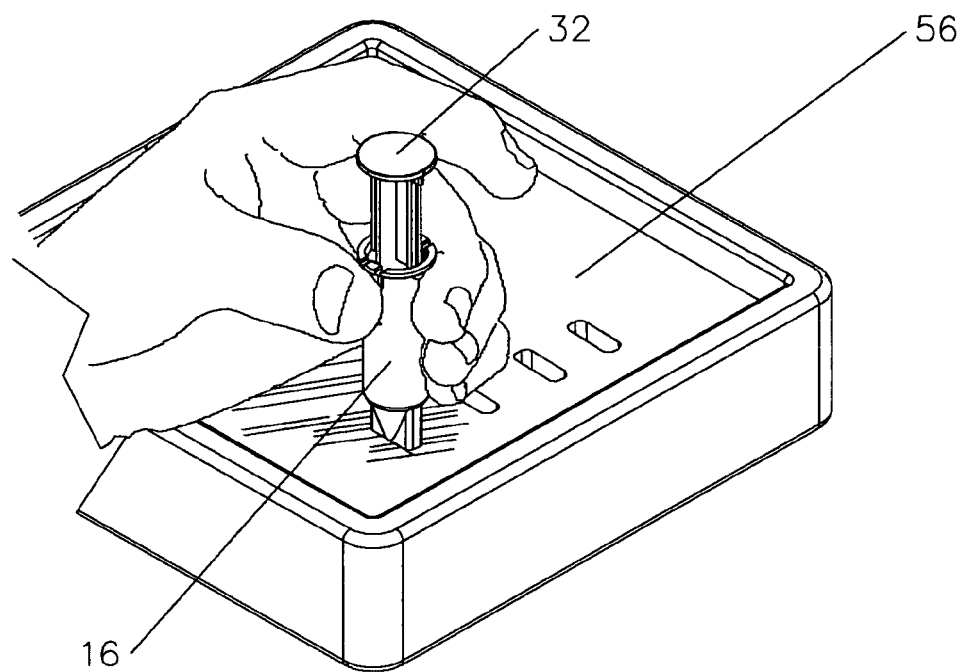
FIG. 7a is a perspective view showing a gel slice extraction.
Figure 7B:
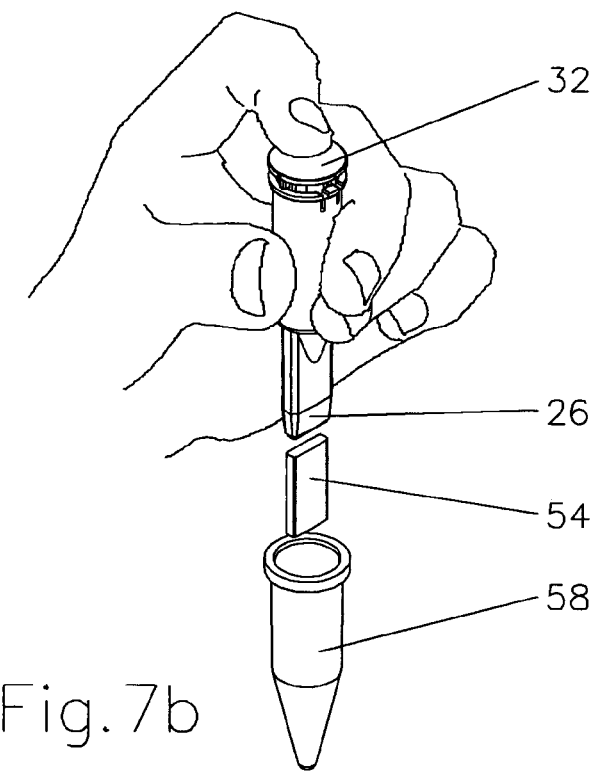
FIG. 7b is a perspective view showing a gel slice transfer.

As seen in FIGS. 7*a* and 7*b*, to extract a gel slice 54, a user in a one handed operation, using a thumb and middle fingers grasps the hollow cutting member 10 proximal tubular body 16 and pushes the gel extraction device 14 downward completely through a gel slab 56. The perimeter cutting edge 28 can be positioned at a variety of angles relative to the gel slab 56 including a preferable 90 degree angle where a clean cut is easily achieved. The downward movement of the gel extraction device 14 causes a gel slice 54 to be transferred and retained by friction force within the tapered end portion 26 of the rectangular receptacle 24. After the cutting step is completed, the gel extraction device 14 still in a resting position is lifted away from the remaining gel slab 56 with the excised gel slice 54 retained in the rectangular receptacle 24 tapered end portion 26 defining distal space 52.

To cause removal of the isolated gel slice 54 from the rectangular receptacle 24 distal space 52 into an open container 58, the gel extraction device 14 is first placed over the open container. Next, the user presses on the gel extraction device 14 proximal end cap 32 compressing the ribbon spring leg 40 and simultaneously moving the outer legs 36 shoulder extension stops 38 where contact occurs with the hollow cutting member 10 circular rim 18 which acts as a stop. At this point, the plunger ejection member 12 solid rectangular distal portion 46 is flush with or slightly past the perimeter cutting edge 28 and the gel slice 54 is removed from the gel extraction device 14. After removal, the user releases pressure on the proximal end cap 32 allowing the compressed ribbon spring leg 40 along with the remaining plunger ejection member 12 to assume a relaxed position as illustrated in FIG. 6.

The gel extraction device 14 does not rely on pressure gradations to retain the gel slice 54. Retention is achieved through frictional forces between the tapered inner walls of the sloped transition portion 22 of the rectangular receptacle 24 and outer walls of the gel slice. Using sharp perimeter cutting edges 28 helps to insure that a clean rectangular gel slice 54 is achieved and that the gel slice 54 is properly seated. Proper seating is required to maximize contact points between the gel slice 54 and the inner walls of the sloped transition portion 22 of the rectangular receptacle 24 so that the gel slice 54 is retained until pressure is applied to the end cap 32 to initiate the gel slice 54 transfer process. This end cap 32 pressure forces the plunger ejector member downward reducing the gel extraction device 14 internal volume thus increasing the internal pressure and ejecting the gel slice 54. FIG. 7*a* shows a gel slice extraction where the gel extraction device 14 is pushed completely through the gel slab 56 at a 90 degree angle. FIG. 7*b* shows the gel extraction device 14 as the gel slice 54 is removed from the sloped transition portion 22 of the rectangular receptacle 24 for deposit into an open container 58.

The gel extraction device 14 perimeter sharp cutting edge 28 is amenable to a wide range of dimensions. For example, where the gel extraction device 14 is used to isolate biomolecules from preparative gels, the dimensions of the device can be varied to accommodate large gel slices. However, the thickness of the cutting edges 28 should not be altered since a clean cut is desirable for all gel slices whether the gel slices are isolated for further analysis of associated biomolecules or for preparative purposes.

In a second embodiment of the present invention as seen in an exploded view in FIG. 8 and assembled in FIG. 9, modified hollow cutting member 10 receives a modified plunger ejector member 12. In this case, the modified plunger ejector member 12 is comprised of the proximal cap 32 atop and connected to a stem portion having a plurality of lateral protrusions 60. The lateral protrusions 60 are at approximately right angles to each other, a pair of oppositely disposed lateral protrusions 60 having proximal shoulder extension stops 38. The lateral protrusions 60 terminate at disk 44, where the solid rectangular distal portion 46 begins.

Figure 11A:
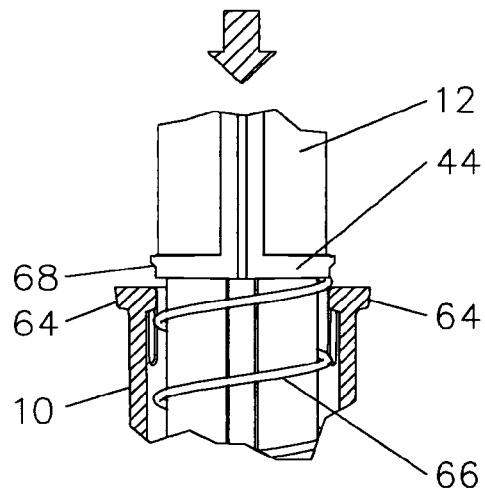
FIGS. 11a, 11b and 11c are partially exposed front views of the plunger ejector member passing through flexible snap locks of a second embodiment of the invention.
Figure 11B:
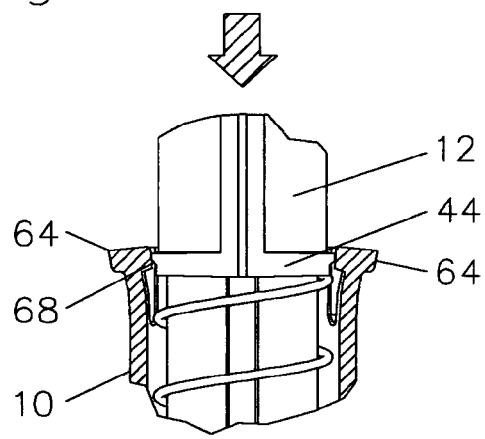
Figure 11C:
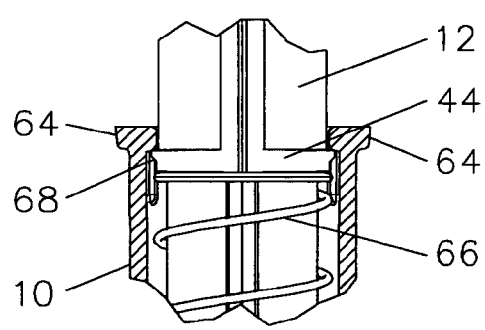

In this embodiment, the modified hollow cutting member 10 has a modified circular rim 18. The modified circular rim 18 has a pair of oppositely positioned flexible snap locks 64 as illustrated in FIGS. 8 and 9. In order to achieve assemblage of the gel extraction device 14 these oppositely positioned flexible snap locks 64 are oriented at 90 degree angles to the rectangular receptacle 24 so that proper modified plunger ejector member 12 insertion can occur. A coiled spring 66 is seated within the modified hollow cutting member 10 tubular body 16. When the modified plunger ejector member 12 is inserted into the hollow cutting member 10, user downward pressure on the proximal cap 32 compresses the coiled spring 66. At this time, the disk 44 passes through the modified circular rim 18 spreading the flexible snap locks 64 outward. Snap lock 64 flexibility is achieved with parallel side cuts from the rim 18 to the tubular body 16 defining a central tab easily moved when pressure is applied. Further plunger ejector member 12 downward movement allows the flexible snap locks 64 to return to their original locking positions. FIG. 10 is a perspective view of the flexible snap locks 64 and FIGS. 11a, 11b and 11c illustrate flexible snap lock 64 action. Also, to provide modified plunger ejector member 12 a smooth entry into the hollow cutting member 10, in this embodiment, the disk 44 has oppositely disposed tapered sections 68 for easy passage through the flexible snap locks 64. Downward plunger ejector member 12 movement ceases when the shoulder extension stops 38 strike the circular rim 18. At this time, the plunger ejector member 12 solid rectangular distal portion 46 projects slightly beyond the hollow cutting member 10 perimeter cutting edge 28 so that a gel slice 54 captured by the cutting member 10 is easily ejected.

Figure 12:
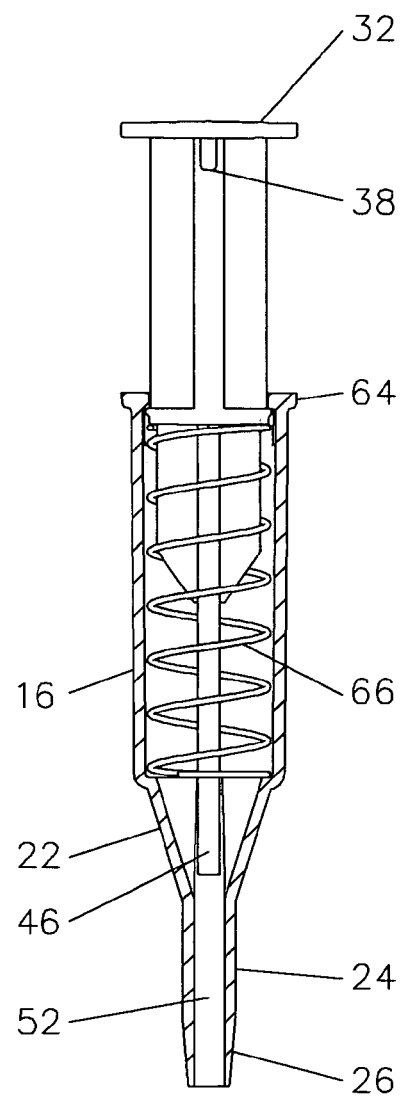
FIG. 12 is a cross section taken along line 12-12 of FIG. 9.

As user pressure is released from the proximal cap 32, the coiled spring 66 relaxes moving the modified plunger ejector member 12 upward until the disk 44 contacts the flexible snap locks 64 where further upward motion is stopped and assemblage of the hollow cutting member 10 and plunger ejector member 12 is effectively maintained. FIG. 12 is a cross section take along line 12-12 of FIG. 9 to show the modified plunger ejector member 12 in a ready position.

In the case of the second embodiment, when an isolated gel slice is removed from the rectangular receptacle 24 distal space 52, the user presses on end cap 32 and now the coiled spring 66 is compressed achieving the same results as ribbon spring leg 40 compression described above. In addition, release of end cap 32 pressure allows the coiled spring 66 to relax as illustrated in FIG. 12.

Figure 15:
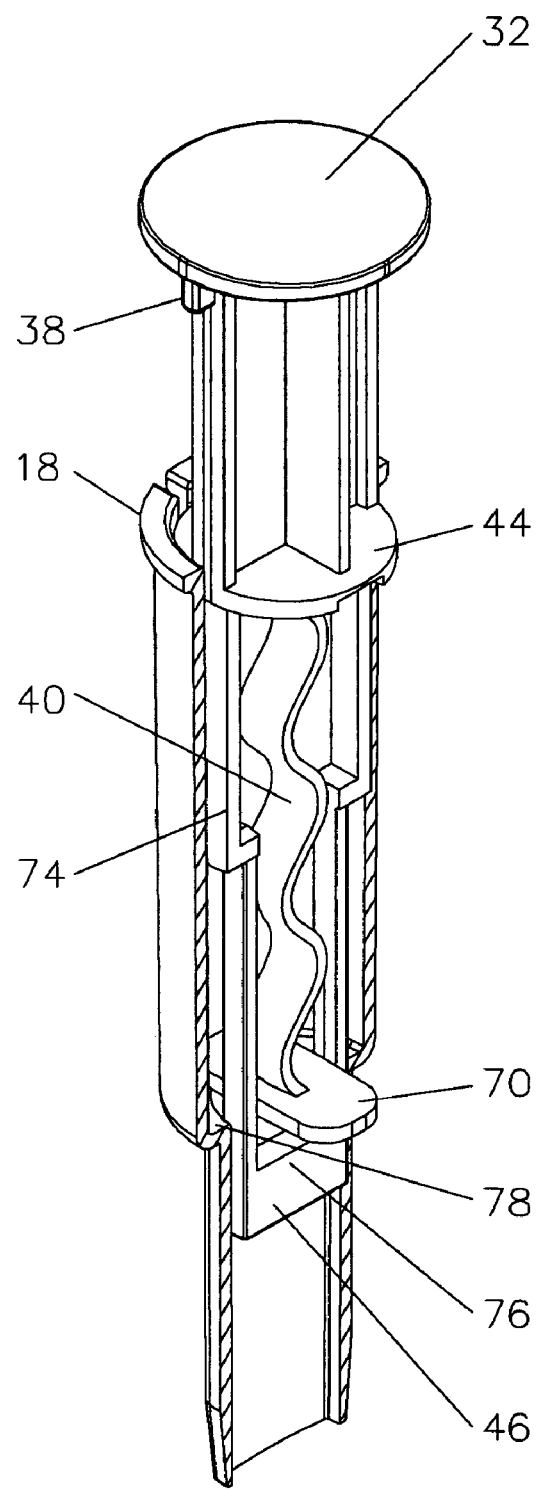
FIG. 15 is a perspective cross section taken through line 15-15 of FIG. 14.

FIG. 13 illustrates an exploded view of the third embodiment of the invention and FIG. 14 shows the assembled invention. Here the plunger ejector member 12 has proximal cap 32 atop and connected to the stem portion having a plurality of lateral protrusions 60 as described above for the second embodiment. However, in this embodiment the plunger ejector member 12 solid rectangular distal portion 46 is modified to include ribbon spring leg 40 having a proximal end affixed to the disk 44 bottom surface and a distal end affixed to an oval piece 70, the ribbon spring leg 40 contained within a rectangular frame 72 opening. The rectangular frame 72 has opposing lateral arms with plunger guides 74 and a bottom frame portion 76 consisting of the solid rectangular distal portion 46. In this embodiment, the hollow cutting member 10 has an internal ledge 78 at the proximal tubular body 16 distal end and is further modified having the modified circular rim 18 with oppositely positioned flexible snap locks 64 as described above for the second embodiment. In this third embodiment, FIG. 14 shows the assembled third embodiment of the gel extraction device 14 and FIG. 15 is a cross section taken through line 15-15 of FIG. 14.

Considering this modified gel extraction device 14 use, when a user applies pressure to the proximal cap 32, the ribbon spring leg 40 compresses until the shoulder extension stops 38 reach the hollow cutting member 10 modified circular rim 18 and the oval piece 70 is resting on the ledge 78. At this time, the solid rectangular portion 46 terminal end extends slightly beyond the hollow cutting member 10 rectangular receptacle 24 perimeter cutting edge 28. Thus proximal cap 32 pressure expels a captured gel slice. As in the second embodiment, as the plunger ejector member 12 travels through the hollow cutting member 10 proximal tubular body 16, the disk 44 passes through the modified circular rim 18 and spreads the flexible snap locks 64 which snap back and retain their original positions to prevent ejection of the plunger ejection member 12 when proximal cap 32 is released and the ribbon spring leg 40 relaxes.

All embodiments of the gel extraction device 14 is preferably made entirely of plastic material such as but not limited to polypropylene, polyethylene, polystyrene or a mixture of plastic materials and the preferred manufacturing method is injection molding. The type of plastic used need not be the same throughout the device. In the second embodiment, the coiled spring 66 is preferably made of stainless steel.

While the present invention has been described in considerable detail, it will be obvious to those skilled in the art that alterations may be made in the device itself or in the procedure for using the device without departing from the concept and scope of the present invention as described in the following claims:

We claim:

1. A gel extraction device comprising
   a hollow cutting member, said hollow cutting member having a proximal tubular body terminating at one end in a circular rim having oppositely disposed spring engaging structures and, continuing from an opposing end of said proximal tubular body, a distal sloped transition portion ending in a rectangular receptacle having a tapered end portion with a perimeter cutting edge; and
   a plunger ejector member, said plunger ejector member having a proximal end cap atop and connected to a split stem portion, said split stem portion having outer legs with shoulder stop extensions and an inner ribbon spring leg having a free distal end, said outer legs terminating at a disk wherein a solid rectangular distal portion begins, said gel extraction device being assembled wherein said plunger ejector member ribbon spring leg free distal end is inserted into a spring engaging structure which acts as a guide to simultaneously direct said solid rectangular distal portion into said hollow cutting member rectangular receptacle.

2. The gel extraction device of claim 1 wherein said rectangular receptacle tapered end portion is formed when opposite short sides and one long side gradually move closer to each other terminating in said perimeter cutting edge.

3. The gel extraction device of claim 2 wherein said perimeter cutting edge is between 0.005 inches to 0.020 inches in thickness.

4. The gel extraction device of claim 1 wherein said ribbon spring leg free distal end has a depression.

5. The gel extraction device of claim 1 wherein said spring engaging structures are oriented at approximately 90 degree angles to said rectangular receptacle.

6. The gel extraction device of claim 5 wherein said spring engaging structure have centrally projected spring locking tabs.

7. A gel extraction device comprising
a modified hollow cutting member, said hollow cutting member having a proximal tubular body terminating at one end in a circular rim having oppositely disposed flexible snap locks and, continuing from an opposing end of said proximal tubular body, a distal sloped transition portion ending in a rectangular receptacle having a tapered end portion with a perimeter cutting edge;
a coiled spring seated within said modified hollow cutting member tubular body; and
a modified plunger ejector member, said modified plunger ejector member having a proximal cap atop and connected to a stem portion having a plurality of lateral protrusions, a pair of oppositely disposed lateral protrusions having proximal shoulder extension stops, said lateral protrusions terminating at a disk wherein a solid rectangular distal portion begins, said modified gel extension device assembled wherein said modified plunger ejector member is inserted into said coiled spring seated within said modified hollow member tubular body and compressed until said disk is below said flexible snap locks.

8. The gel extraction device of claim 7 wherein said flexible snap locks have an easily moved central tab.

9. The gel extraction device of claim 7 wherein said rectangular receptacle tapered end portion is formed when opposite short sides and one long side gradually move closer to each other terminating in said perimeter cutting edge.

10. The gel extraction device of claim 9 wherein said perimeter cutting edge is between 0.005 inches to 0.020 inches in thickness.

11. The gel extraction device of claim 7 wherein said disk has oppositely disposed tapered sections.

12. The gel extraction device of claim 7 wherein said lateral protrusions are oriented at approximately 90 degree angles to each other.

13. The gel extraction device of claim 7 wherein said coiled spring is made of stainless steel.

14. A gel extraction device comprising
a modified hollow cutting member, said hollow cutting member having a proximal tubular body terminating at one end in a circular rim having oppositely disposed flexible snap locks and, continuing from an opposing end of said proximal tubular body, a distal sloped transition portion ending in a rectangular receptacle having a tapered end portion with a perimeter cutting edge, said hollow cutting member tubular body having an internal ledge within a tubular body distal end; and
a modified plunger ejector member, said modified plunger ejector member having a proximal cap atop and connected to a stem portion having a plurality of lateral protrusions, a pair of oppositely disposed lateral protrusions having proximal shoulder extension stops, said lateral protrusions terminating at a disk wherein a ribbon spring leg, affixed to a disk bottom surface has a distal end affixed to an oval piece, said ribbon spring leg contained within a rectangular frame opening, said rectangular frame having opposing lateral arms with plunger guides and a bottom frame portion having a solid rectangular distal portion, said gel extraction device assembled when said modified plunger ejector member is inserted into said modified hollow cutting member until said oval piece is resting on said ledge and said disk is below said flexible snap locks.

15. The gel extraction device of claim 14 wherein said flexible snap locks have an easily moved central tab.

16. The gel extraction device of claim 14 wherein said rectangular receptacle tapered end portion is formed when opposite short sides and one long side gradually move closer to each other terminating in said perimeter cutting edge.

17. The gel extraction device of claim 16 wherein said perimeter cutting edge is between 0.005 inches to 0.020 inches in thickness.

18. The gel extraction device of claim 14 wherein said disk has oppositely disposed tapered sections.

19. The gel extraction device of claim 14 wherein said lateral protrusions are oriented at approximately 90 degree angles to each other.

* * * * *